United States Patent
Zhu et al.

(10) Patent No.: US 11,058,703 B2
(45) Date of Patent: Jul. 13, 2021

(54) APPLICATION OF TRIACETYL-3-HYDROXYPHENYLADENOSINE IN PREPARATION OF PHARMACEUTICAL DRUG FOR PREVENTING OR TREATING NON-ALCOHOLIC FATTY LIVER DISEASE

(71) Applicants: JIANGSU TASLY DIYI PHARMACEUTICAL CO., LTD, Jiangsu (CN); INSTITUTE OF MATERIA MEDICA, CHINESE ACADEMY OF MEDICAL SCIENCES, Beijing (CN)

(72) Inventors: Haibo Zhu, Jiangsu (CN); Huijie Shi, Jiangsu (CN)

(73) Assignees: Jiangsu Tasly Diyi Pharmaceutical Co., Ltd., Jiangsu (CN); Institute of Materia Medica, Chinese Academy of Medical Sciences, Beijing (CN)

( * ) Notice: Subject to any disclaimer, the term of this patent is extended or adjusted under 35 U.S.C. 154(b) by 64 days.

(21) Appl. No.: 16/067,228

(22) PCT Filed: Dec. 28, 2016

(86) PCT No.: PCT/CN2016/112623
§ 371 (c)(1),
(2) Date: Jun. 29, 2018

(87) PCT Pub. No.: WO2017/114413
PCT Pub. Date: Jul. 6, 2017

(65) Prior Publication Data
US 2019/0022120 A1    Jan. 24, 2019

(30) Foreign Application Priority Data
Dec. 31, 2015 (CN) .......................... 201511034199.0

(51) Int. Cl.
*A61K 31/7076* (2006.01)
*A61P 1/16* (2006.01)

(52) U.S. Cl.
CPC ............ *A61K 31/7076* (2013.01); *A61P 1/16* (2018.01)

(58) Field of Classification Search
CPC ........................... A61P 1/16; A61K 31/7076
See application file for complete search history.

(56) References Cited

U.S. PATENT DOCUMENTS

| 8,435,962 B2 | 5/2013 | Zhu et al. | |
| 2019/0070208 A1* | 3/2019 | Zhu ................... | A61K 31/7076 |

FOREIGN PATENT DOCUMENTS

| AU | 2013204500 A1 | 4/2014 |
| CN | 101874036 A | 10/2010 |
| CN | 102125580 A | 7/2011 |
| CN | 105663152 | 6/2016 |
| EP | 2407474 A1 | 1/2012 |
| WO | 2010040286 A1 | 4/2010 |
| WO | 2014153919 A1 | 10/2014 |
| WO | 2015002818 A1 | 1/2015 |

OTHER PUBLICATIONS

Sharabi et al., "Nonalcoholic Fatty Liver Disease is Assdociated with Hyperlipidemia and Obesit,." The American Journal of Medicine, 109(2), 171 (Aug. 1, 2000).*
Chinese Search Report dated Mar. 24, 2017, PCT/CN2016/112623.
European Search Report and Written Opinion dated May 9, 2019, Appl. SN 16 881 202.2.
Lian et al., "A novel AMPK activator, WS070117, improves lipid metabolism discords in hamsters and HepG2 cells", Lipids in Health and Disease, 2011, 10:67 pp. 1-8.
Chemical Encyclopedia, N.S. Zeifirova Publishing House; "Bolshaya Russian Encyclopedia", 1995, 4: 376-377.
Second Russian Office Action dated Jun. 10, 2020.
Japanese Office Action dated Oct. 20, 2020 with the English Translation.
Sun et al.; "Beneficial Metabolic Effects of 2',3',5'-tri-acetyl-N6-(3-Hydroxylaniline) Adenosine in the Liver and Plasma of Hyperlipidemic Hamsters"; 7(3): 2012.

* cited by examiner

*Primary Examiner* — Lawrence E Crane
(74) *Attorney, Agent, or Firm* — Dilworth & Barrese, LLP

(57) ABSTRACT

The present invention provides an application of triacetyl-3-hydroxyphenyladenosine represented by formula (I) in preventing or treating non-alcoholic fatty liver disease. The triacetyl-3-hydroxyphenyladenosine can significantly reduce the levels of serum AST, ALT and TG, significantly improve liver functions, and alleviate liver steatosis. The invention provides significant curative effects for preventing or treating non-alcoholic fatty liver and has limited toxic side effects.

9 Claims, 3 Drawing Sheets

APPLICATION OF TRIACETYL-3-HYDROXYPHENYLADENOSINE IN PREPARATION OF PHARMACEUTICAL DRUG FOR PREVENTING OR TREATING NON-ALCOHOLIC FATTY LIVER DISEASE

CROSS-REFERENCES TO RELATED APPLICATIONS

This application is a U.S. National Stage Application under 35 U.S.C. § 371 of International Application No. PCT/CN2016/112623 filed on Dec. 28, 2016, which claims priority under 35 U.S.C. § 119(b) to Chinese Patent Application No. 201511034199.0 filed on Dec. 31, 2015, the entire contents of which is incorporated herein by reference.

TECHNICAL FIELD

The invention relates to an application of triacetyl-3-hydroxyphenyladenosine and a pharmaceutical composition containing the same in the preparation of a pharmaceutical drug for preventing or treating non-alcoholic fatty liver disease, which belongs to the technical field of medicine.

BACKGROUND

Non-alcoholic fatty liver disease (NAFLD) refers to a group of clinical pathological syndromes characterized by liver parenchymal cell damage and fat accumulation caused by other than excessive alcohol consumption and other definite pathogenesis of liver damage, which is a metabolically-stressed liver damage closely related to insulin resistance (IR) and genetic susceptibility, and the pathological changes of which are similar to those of alcoholic liver disease, but the patient has no history of excessive drinking. Its components include non-alcoholic simple fatty liver (NAFL), non-alcoholic steatohepatitis (NASH), non-alcoholic fatty liver fibrosis, non-alcoholic fatty liver cirrhosis, and related hepatic carcinoma (HCC). With the development of our country's economy, the content and time of people's diet have changed a lot, and the incidence of non-alcoholic fatty liver disease has been continuously rising, and trends in young person, which has become a common disease that seriously threatens the physical and psychological health of human beings.

The exact pathogenesis of NAFLD is still unclear, and it is generally accepted as the "two hit" theory, the first hit in the two phases of the theory is that a decrease in the amount of decomposition and excessive intake of high-fat diet results in lipid deposition and the formation of simple fatty liver. In the two hit, IR can weaken and destroy the regulation of insulin on fat metabolism, increase lipid lysis, increase non-esterified free fatty acid (FFA) concentration, and promote liver uptake of FFA in the blood. Oxidative stress and lipid peroxidation injury play an important role in the formation and development of fatty liver, which is an important factor in the further development of fatty liver by the second hit. Mitochondrion is a respiratory organ of cells, the increased generation of reactive oxygen species (ROS) damages the mitochondrion, further accelerating lipid accumulation in the liver. In addition, the free radicals produced by oxidative stress cause the damage reaction of lipid peroxidation (LPO), form a series of lipid radicals and degradation products—malondialdehyde (MDA), at the same time, destroy the structure and function of the biomembrane, increase the permeability of the cell membrane, cause the cytochrome C to flow out, initiate the apoptosis program, and finally lead to liver fibrosis, liver cirrhosis, and even to hepatic carcinoma. At present, there is still a lack of specific drugs. Commonly used lipid-lowering drugs such as statins and fibrates have poor efficacy and great toxic and side effect.

Triacetyl-3-hydroxyphenyladenosine (Patent No. ZL200980101131.6, Publication No. CN101874036B, Notice Date 2012 Jan. 25) is a new structural type compound with significant lipid regulating activity screened in cordycepin derivatives by the Institute of Materia Medica, Chinese Academy of Medical Sciences, and has the characteristics of small toxic and side effects and good pharmacokinetics, etc., which is currently in the pre-clinical research stage. There is no report on the application of this compound in the prevention or treatment of non-alcoholic fatty liver disease.

SUMMARY OF THE INVENTION

The technical problem solved by the present invention is to provide an application of a compound triacetyl-3-hydroxyphenyladenosine and a pharmaceutical composition thereof in the preparation of a pharmaceutical drug for preventing or treating non-alcoholic fatty liver disease.

In order to solve the technical problem of the present invention, the following technical solution is provided:

a first aspect of the technical solution of the present invention is to provide an application of triacetyl-3-hydroxyphenyladenosine represented by formula (I) and a pharmaceutically acceptable salt thereof in the preparation of a pharmaceutical drug for preventing or treating non-alcoholic fatty liver disease,

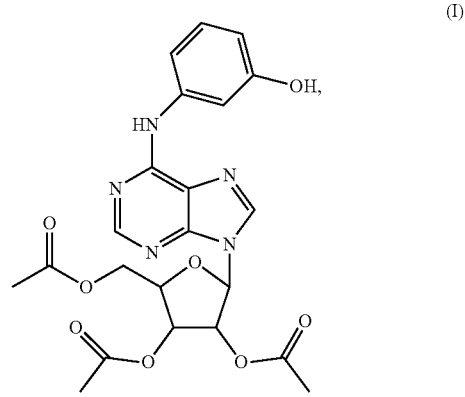 [SMILES: CC(=O)OCC1OC(n2cnc3c(Nc4cccc(O)c4)ncnc32)C(OC(C)=O)C1OC(C)=O]

the non-alcoholic fatty liver disease is fatty liver disease caused by a high-calorie diet, the treatment of non-alcoholic fatty liver disease with the triacetyl-3-hydroxyphenyladenosine of the present invention is that it can significantly reduce the levels of serum aspartate aminotransferase (AST), alanine aminotransferase (ALT) and triglyceride (TG), significantly improve liver function of a golden hamster with fatty liver disease, reduce the degree of fatty liver, thereby preventing or treating non-alcoholic fatty liver disease. A second aspect of the technical solution of the present invention is to provide an application of a pharmaceutical composition in the preparation of a pharmaceutical drug for preventing or treating non-alcoholic fatty liver disease, characterized in that, the pharmaceutical composition comprises triacetyl-3-hydroxyphenyladenosine represented by formula (I) and a pharmaceutically acceptable salt thereof and a pharmaceutically acceptable carrier,

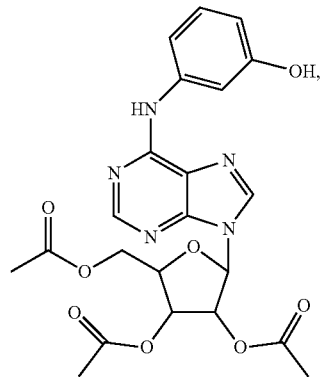

(I)

the pharmaceutical composition includes a tablet, a capsule, a pill and an injection, a sustained release formulation, a controlled release formulation or various microparticle drug delivery systems. The pharmaceutical composition can be prepared according to methods known in the art. Any dosage form suitable for human or animal use may be made by combining the compound of the present invention with one or more pharmaceutically acceptable solid or liquid excipients and/or adjuvants. The content of the compound of the present invention in the pharmaceutical composition thereof is usually from 0.1 to 95% by weight.

The compound or the pharmaceutical composition containing the same of the present invention may be administered in unit dosage form, and the administration route may be intestinal or parenteral, such as oral, intravenous, intramuscular, subcutaneous, nasal, oral mucosa, eyes, lung and respiratory tract, skin, vagina, rectum, and the like.

The administration dosage form may be liquid, solid or semi-solid dosage forms. The liquid dosage forms may be solutions (including true solutions and colloidal solutions), emulsions (including o/w type, w/o type, and double emulsions), suspensions, injections (including water injections, powder injections and infusions), eye drops, nose drops, lotions, and liniments, etc.; the solid dosage forms may be tablets (including common tablets, enteric-coated tablets, lozenges, dispersible tablets, chewable tablets, effervescent tablets, orally disintegrating tablets), capsules (including hard capsules, soft capsules, enteric-coated capsules), granules, powders, mini-pills, dripping pills, suppositories, films, patches, (power) aerosols, sprays, and the like; and the semi-solid dosage forms may be ointments, gels, pastes, and the like. The preferred dosage form of the pharmaceutical composition is selected from the group consisting of tablets, capsules, pills, and injections.

The compound of the present invention can be prepared into ordinary preparations, also made into sustained release preparations, controlled release preparations, targeting preparations, and various microparticle drug delivery systems.

In order to prepare the compound of the present invention into tablets, various excipients known in the art can be widely used, including diluents, binders, humectants, disintegrants, lubricants, and glidants. The diluent may be starch, dextrin, sucrose, glucose, lactose, mannitol, sorbitol, xylitol, microcrystalline cellulose, calcium sulfate, calcium hydrogen phosphate, calcium carbonate, and the like; the humectant may be water, ethanol, isopropanol, and the like; the binder may be starch slurry, dextrin, syrup, honey, glucose solution, microcrystalline cellulose, mucilago acaciae, gelatin slurry, sodium carboxymethylcellulose, methylcellulose, hydroxypropyl methyl cellulose, ethyl cellulose, acrylic resin, carbomer, polyvinylpyrrolidone, polyethylene glycol, and the like; the disintegrant may be dry starch, microcrystalline cellulose, low-substituted hydroxypropyl cellulose, crospolyvinylpyrrolidone, croscarmellose sodium, sodium carboxymethyl starch, sodium hydrogen carbonate and citric acid, polyoxyethylene sorbitol fatty acid ester, sodium dodecyl sulfate, and the like; and the lubricant and the glidant may be talc, silica, stearate, tartaric acid, liquid paraffin, polyethylene glycol, and the like.

The tablets may also be further prepared into coated tablets, such as a sugar-coated tablets, film-coated tablets, enteric coated tablets, or double-layer tablets and multilayer tablets.

In order to formulate the dosing unit into capsules, the active ingredient, the compound of the present invention, may be mixed with a diluent, a glidant, and the mixture may be placed directly in a hard or soft capsule. The active ingredient, the compound of the present invention, may also be first prepared into granules or mini-pills with a diluent, binder, or disintegrant, and then placed in a hard or soft capsule. A wide variety of diluents, binders, humectants, disintegrants, glidants for the preparation of tablets of the compound of the present invention may also be used in the preparation of capsules of the compound of the present invention.

In order to prepare the compound of the present invention into injections, water, ethanol, isopropanol, propylene glycol, or a mixture thereof may be used as a solvent and added with an appropriate amount of solubilizers, solubilizers, pH adjusting agents, osmotic pressure regulators commonly used in the art. The solubilizer or glidant may be poloxamer, lecithin, hydroxypropyl-beta-cyclodextrin, and the like; the pH adjusting agent may be phosphate, acetate, hydrochloric acid, sodium hydroxide, and the like; and the osmotic pressure regulator may be sodium chloride, mannitol, glucose, phosphate, acetate, and the like. For preparing freeze-dried powder injections, mannitol, glucose, and the like may also be added as a proppant.

In addition, colorants, preservatives, perfumes, corrigents, or other additives may also be added to the pharmaceutical preparation as needed.

In order to achieve the purpose of medication and enhance the therapeutic effect, the pharmaceutical or pharmaceutical composition of the present invention may be administered by any known method of administration.

The dosage of the pharmaceutical composition of the compound of the present invention may vary depending on the nature and severity of the disease to be prevented or treated, the individual condition of the patient or animal, the route of administration and the dosage form, and the like. In general, suitable daily dosage for the compound of the invention may range from 0.001 to 150 mg/kg body weight, preferably 0.1 to 100 mg/kg body weight, more preferably 1 to 60 mg/kg body weight, and most preferably 2 to 30 mg/kg body weight. The above dosages can be administered in one dosage unit or divided into several dosage units, depending on the clinician's clinical experience and dosage regimen including the use of other treatment means.

The compound or composition of the present invention may be administered alone or in combination with other therapeutic drugs or symptomatic drugs. When the compound of the present invention has a synergistic effect with other therapeutic drugs, its dosage should be adjusted according to actual conditions.

Beneficial Technical Effect

The present invention has confirmed the significant effect of triacetyl-3-hydroxyphenyladenosine in the prevention or treatment of non-alcoholic fatty liver disease using pharmacodynamics research methods, which provides a new preventive or therapeutic drug, triacetyl-3-hydroxyphenyladenosine, for this chronic disease with complicated pathogenesis and poor therapeutic effect, with obvious curative effect, little toxic and side effects and safe use, and provides scientific basis for clinical application in the prevention or treatment of non-alcoholic fatty liver disease.

DESCRIPTION OF THE DRAWINGS

In order to make the content of the present invention more clearly understood, the present invention is further described in detail in the following with reference to specific embodiments of the present invention and with reference to the accompanying drawings, wherein.

DETAILED DESCRIPTION OF THE INVENTION

Figure 1:
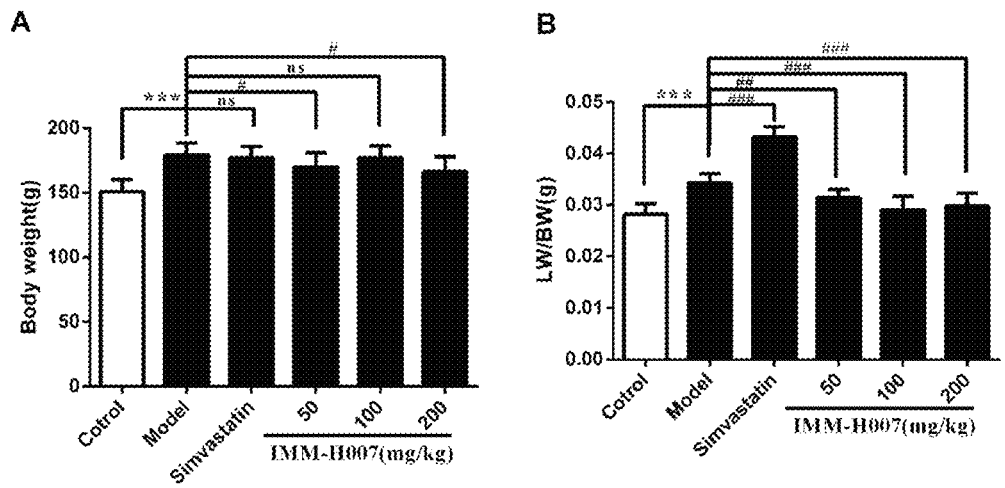
FIG. 1 is a comparison of body weight and liver coefficient of golden hamsters of each group in the experimental example of the present invention.

The following examples are intended to further illustrate the present invention, but are not meant to limit the present invention in any way.

Example 1

Application of Tracetyl-3-Hydroxyphenyladenosine (IMM-H007) in the Treatment of Non-Alcoholic Fatty Liver Disease I. Experimental Materials
1. Reagents OCT frozen section embedding agent, SAKURA Tissue-Tek®; pentobarbital sodium, SIGMA; PEG6000, SIGMA; glycine, SIGMA; paraformaldehyde, Sinopharm Chemical ReagentCo., Ltd; Oil Red O, SIGMA; HE staining solution, Taiwan Baso Corporation; total cholesterol (TC) detection kit, Sekisui Medical Technology (China) LTD; total triglyceride detection kit, BioSino Bio-Technology & Science Inc.; free fatty acid detection kit, Sekisui Medical Technology (China) LTD; glutamic-pyruvic transaminase (AST/ALT) detection kit, Nanjing Jiancheng Bioengineering Institute; glutamic oxalacetic transaminase (AST/GOT) detection kit, Nanjing Jiancheng Bioengineering Institute.

2. Instruments

Multi-purpose low-temperature high-speed centrifuge, Eppendorff, Germany; paraffin microtome, Leica, Germany; frozen microtome, Leica, Germany; En Vision multimode reader, PerkinElmer, Inc., USA; small animal anaesthesia machine, Matrx Products, USA; small animal magnetic resonance imaging machine, Bruker PharmaScan 70T/16 US, Germany.

3. Experimental Animals 6 to 8-week-old Syrian golden hamsters (LVG hamster, imported from Charles River Laboratories), 20, weighing 90-120 g, male, SPF grade, purchased from Beijing Vital River Laboratory Animal Technology Co., Ltd., and license number: SCXK (Beijing) 2012-0001.

II. Experimental Methods
1. Animal Grouping and Rearing

After 5 days of adaptive feeding, animals were randomly divided into a normal control group (n=15), a high-fat diet group (n=15), an IMMH007 low-dose group (25 mg/kg, n=15), an IMMH007 medium-dose group (50 mg/kg, n=15), and an IMMH007 high-dose group (100 mg/kg, n=15), and given intragastric administration twice daily. The animals were reared in the Animal Experiment Center II of the Institute of Materia Medica, Chinese Academy of Medical Sciences, and the rearing conditions were SPF grade, temperature of 21±2° C., relative humidity of 50±5%, light cycle of 12/112, and 5 per cage. The normal group was given normal basal diet, and the high-fat diet group was given high-fat diet (79.8% basal diet added with 20% lard and 0.2% cholesterol), and the animals were allowed to eat and drink freely. The feed was commissioned by Beijing HFK Bioscience Co., Ltd. Body weight was recorded every 2 weeks during the experiment.

2. Observation Indicators and Measurement Methods
2.1 Serum Biochemical Indicators The animals were fasted for 12 hours, and 0.5 ml blood was collected from the angular vein and allowed to stand for 60 min, and centrifuged at 6000 g for 10 min, and the supernatant was aspirated as much as possible, and then centrifuged at 6000 g for 10 min. The absorbance values were measured according to the instructions of the total cholesterol (TC), triglycerides (TG), aspartate aminotransferase (AST), and alanine aminotransferase (ALT) kits, and the concentration of each index was calculated. 50 ul serum was mixed with 50 ul PEG6000 in a ratio of 1:1, vortexed uniformly, allowed to stand for 10 min, and centrifuged at 1900 g for 20 min at room temperature, and the supernatant was carefully pipetted, stored at 4° C., and measured for high density lipoprotein cholesterol (HDL-C) according to the instructions of the total cholesterol (TC) kit. The plasma low density lipoprotein (LDL) level was calculated by subtracting HDL-C and 0.2-fold TG levels from plasma total cholesterol TC, ie, LDL=TC-HLD-0.2TG.

The animals were fasted overnight before the end of the experiment, anesthetized by intraperitoneal injection of 3% pentobarbital sodium, the abdominal cavity was exposed, and the liver was rapidly separated after blood was taken from the aorta abdominalis. One liver lobe was preserved, and two pieces of 1×1 $cm^3$ pieces were cut at a fixed site, one piece was embedded in OCT, quickly frozen in liquid nitrogen, and stored in liquid nitrogen or at −80° C.; and the other piece was placed in a 4% paraformaldehyde stationary liquid and stored at 4° C.

2.2 Magnetic Resonance Imaging

After being fasted for 12 hours, the animals were anesthetized with isoflurane, fixed on their heads, and supine and fixed on the rat's coil, the head entered first, and the center of the abdomen was positioned.

T2-weighted imaging (T2WI) of the fast spin echo sequence: TR/TE=200/3 ms, FA=30°. Field of view (FOV) =3.6×3.6, matrix=256×256, and number of excitations=2 times.

2.2 Analysis of Lipid Content in Liver Tissue 100 mg liver tissue was accurately weighed, and added with a triglyceride detection lysate, the tissue was homogenized by a homogenizer in an ice bath to no significant tissue mass, placed on ice for 5 min, transferred to a 1.5 ml centrifuge tube, and centrifuged at 14000 g for 10 min at 4° C., the supernatant was transferred and a portion of the supernatant was taken for protein quantification, and detected for its lipid content according to the instructions of the TC and TG detection kits.

2.3 Pathological Staining of Liver Tissue 2.3.1 Preparation of Paraffin Sections The liver fixed with paraformaldehyde stationary liquid was rinsed with tap water and dehydrated in the following steps, with 70% ethanol overnight, 80% ethanol overnight, 90% ethanol I for 30 min, 90% ethanol II for 30 min, 95% ethanol I for 60 min, 95% ethanol II for 60 min, 100% ethanol I for 60 min, and 100% ethanol II for 60 min, and the dehydration time for normal tissues can be appropriately extended. After dehydration, the tissue was transparentized with Super-safety and environmental-protection transparent agent, Super-safety and environmental-protection transparent agent I for 60 min, Super-safety and environmental-protection transparent agent II for 60 min, and Super-safety and environmental-protection transparent agent III for 60 min, and the transparentization time for normal tissues can be appropriately extended. The tissue was immersed in wax at 65° C., paraffin I for 50 min, paraffin II for 50 min, and paraffin III for 50 min, embedded, sliced at a thickness of 7 μm, exposed at 45° C., and baked overnight at 50° C.

2.3.2 Preparation of Frozen Sections

Before the liver tissue was sectioned, the temperature of a freezer of a microtome was set to −19° C. and the sample head was set to −21° C. The liver stored in liquid nitrogen or −80° C. was preliminarily equilibrated at −20° C., and then the tissue was placed on a sample stand of the microtome for temperature equilibration. After the tissue block was trimmed, the tissue block was serially sectioned to a thickness of 7 μm and applied to a clean polylysine-coated slide.

2.3.3 Oil Red O Staining

The frozen section was fixed in 4% paraformaldehyde physiological solution for 10 min, rinsed with tap water for 2 min, rinsed with 60% isopropanol for several seconds, stained with 0.5% Oil Red O working droplets for 10-15 min in a light-proof staining box, separated by 60% isopropanol for several seconds, washed gently with tap water, counterstained with hematoxylin for 3-5 min, differentiated with 1% hydrochloric acid in water, rinsed with tap water for 2 min and returned to blue, sealed with glycerol gelatin and observed under a microscope.

2.3.4 HE Staining

The paraffin section was dehydrated in the following steps with Super-safety and environmental-protection transparent agent I for 5 min, Super-safety and environmental-protection transparent agent II for 5 min, Super-safety and environmental-protection transparent agent for 5 min, 100% ethanol I for 3 min, 100% ethanol II for 3 min, 95% ethanol I for 3 min, 95% ethanol II for 3 min, and 80% ethanol for 3 min, and rinsed with tap water for 1 min, stained with hematoxylin for 5 min, washed with tap water for 1 min, differentiated with 1% hydrochloric acid in ethanol for several seconds, rinsed with tap water and returned to blue, rinsed in 80% ethanol for several seconds, stained with eosin for 10 seconds, toned with 80% ethanol and 95% ethanol, dehydrated, ie, with 95% ethanol, 100% ethanol I, 100% ethanol II, Super-safety and environmental-protection transparent agent I, Super-safety and environmental-protection transparent agent II, and Super-safety and environmental-protection transparent agent III 60 for 2 min each, sealed with ultra-clean high-grade mounting glue and observed under a microscope.

3. Data Analysis

The data were expressed as mean value±standard error, and all data were statistically analyzed by ONEWAY-ANOVA using Graphpad Prism 5.0 software; the images were compared and analyzed.

III. Experimental Results 3.1 Effect of IMM-H007 on Body Weight and Liver Coefficient of Golden Hamster with Non-alcoholic Fatty Liver Disease Induced by High-fat Diet From Table 1 and FIG. 1, it can be seen that compared with golden hamsters in the normal group, the body weight of the golden hamster in the model group increased significantly, and their liver coefficient increased; and compared with the model group, both body weight and liver coefficient decreased after treatment with administration of IMM-H007. However, after treatment with administration of simvastatin, the liver coefficient of golden hamsters did not decrease but increased significantly.

TABLE 1

Effect of IMM-H007 on Body Weight and Liver Coefficient of Golden Hamster with Chronic Fatty Liver

| Group (n = 10) | Dose mg/kg | Body Weight | Liver Organ Coefficient |
| --- | --- | --- | --- |
| Normal Group | — | 150 ± 9 | 0.0282 ± 0.002 |
| Model Group | — | 180 ± 9*** | 0.0340 ± 0.002*** |
| Simvastatin Group | 3 | 177 ± 9 | 0.0433 ± 0.002### |
| IMM-H007 | 50 | 170 ± 11# | 0.0313 ± 0.002## |
|  | 100 | 177 ± 9 | 0.0291 ± 0.003### |
|  | 200 | 166 ± 12# | 0.0298 ± 0.002### |

Figure 2:
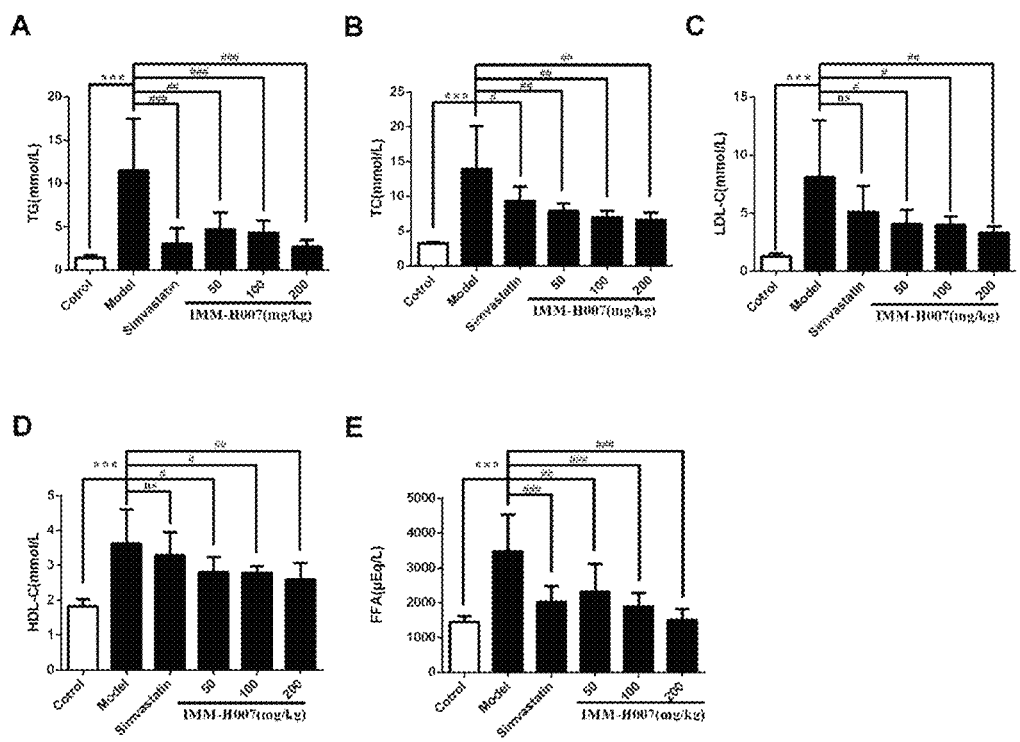
FIG. 2 is a comparison of the determination results of content of cholesterol, triglyceride, high-density lipoprotein, low-density lipoprotein, and free fatty acid in the serum of golden hamsters in the experimental example of the present invention.

***$P < 0.001$, compared with normal group;
$p < 0.001$,
$p < 0.01$,
$p < 0.05$ compared with model group 3.2 Effect of IMM-H007 on Serum Lipid Indexes in Serum of Golden Hamster with Non-alcoholic Fatty Liver Disease Induced by High-fat Diet Compared with the golden hamsters in the normal group, the TC, TG, LDL-C, HDL-C and FFA in the serum of the golden hamsters in the model group were significantly increased; and compared with the model group, the TC, TG, LDL-C, HDL-C, and FFA were significantly reduced after administration of IMM-H007 (Table 2 and FIG. 2).

TABLE 2

Effect of IMM-H007 on Serum Lipid Indexes in Serum of Golden Hamster with non-alcoholic fatty liver disease Induced by High-fat Diet

| Group (n = 10) | Dose mg/kg | TC (mmol/L) | TG (mmol/L) | LDL-C (mmol/L) | HDL-C (mmol/L) | FFA µEq/L |
|---|---|---|---|---|---|---|
| Normal Group | — | 3.3 ± 0.17 | 1.4 ± 0.3 | 1.3 ± 0.3 | 1.8 ± 0.2 | 1444.8 ± 173.8 |
| Model Group | — | 14.0 ± 6.2*** | 11.5 ± 6.0*** | 8.1 ± 4.9*** | 3.6 ± 1.0*** | 3468.4 ± 1058.1*** |
| Simvastatin Group | 3 | 9.4 ± 2.1# | 3.1 ± 1.8### | 5.1 ± 2.3 | 3.3 ± 0.7 | 2013.6 ± 457.6### |
| IMM-H007 | 50 | 7.9 ± 1.0## | 4.7 ± 1.9## | 4.1 ± 1.2# | 2.8 ± 0.4# | 2324.6 ± 783.4# |
|  | 100 | 7.0 ± 1.0## | 4.3 ± 1.4## | 4.0 ± 0.7# | 2.8 ± 0.2# | 1889.5 ± 386.5### |
|  | 200 | 6.7 ± 1.0## | 2.7 ± 0.8### | 3.3 ± 0.5# | 2.6 ± 0.5## | 1497.6 ± 326.2### |

***P < 0.001, compared with normal group;
P < 0.001,
P < 0.01,
P < 0.05 compared with model group

Figure 3:
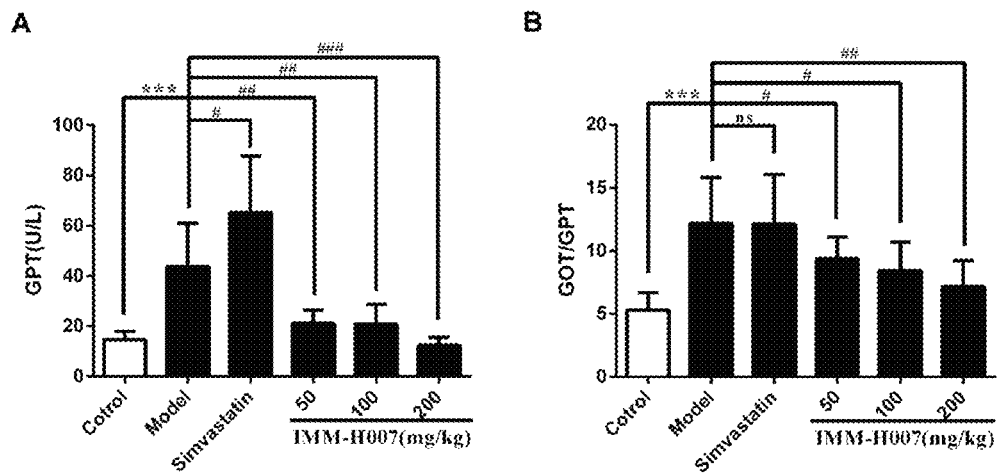
FIG. 3 is a comparison of ALT and AST enzyme activity of golden hamsters in the experimental example of the present invention.

3.3 Effect of IMM-H007 on Liver Function of Golden Hamster with Non-alcoholic Fatty Liver Disease Induced by High-fat Diet As can be seen from Table 3, the levels of glutamic-pyruvic transaminase and glutamic oxalacetic transaminase in the serum of the golden hamsters in the model group were significantly increased, and the serum ALT and AST were significantly decreased after treatment with IMM-H007. However, after treatment with administration of simvastatin, there was no decrease in glutamic-pyruvic transaminase but significant increase (Table 3 and FIG. 3); while there was no significant difference between the level of glutamic oxalacetic transaminase and that of the model group, suggesting that IMM-H007 has a good hepatic protective effect, but simvastatin shows the effect of damaging the liver.

TABLE 3

Effect of IMM-H007 on ALT, AST levels in Serum of Golden Hamster with non-alcoholic fatty liver disease Induced by High-fat Diet

| Group (n = 10) | Dose mg/kg | GPT (U/L) | GOT (U/L) |
|---|---|---|---|
| Normal Group | — | 14.7 ± 3.3 | 5.3 ± 1.4 |
| Model Group | — | 43.7 ± 17.2*** | 12.2 ± 3.6*** |
| Simvastatin Group | 3 | 65.2 ± 22.5# | 12.1 ± 4.0 |
| IMM-H007 | 50 | 21.1 ± 5.2## | 9.4 ± 1.7# |
|  | 100 | 20.9 ± 8.0## | 8.4 ± 2.3# |
|  | 200 | 12.4 ± 3.1### | 7.2 ± 2.1## |

***P < 0.001, compared with normal group;
P < 0.001,
P < 0.01,
P < 0.05 compared with model group

Figure 4:
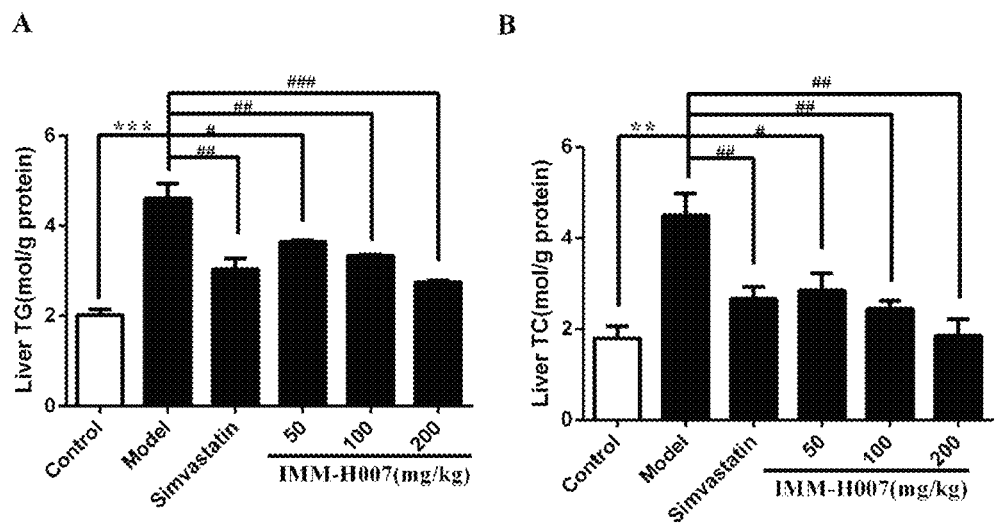
FIG. 4 is a comparison of the determination results of lipid contents in liver tissues of golden hamsters of each group in the experimental example of the present invention.

3.4 Effect of IMM-H007 on Hepatic Lipid Changes in Golden Hamster with Non-alcoholic Fatty Liver Disease Induced by High-fat Diet From Table 4 and FIG. 4, it can be seen that compared with the golden hamsters in the normal group, TC and TG in the liver of the golden hamsters in the model group were significantly increased; and compared with the model group, TC and TG were significantly reduced after simvastatin and IMM-H007 were given.

TABLE 4

Effect of IMM-H007 on Hepatic Lipid Changes in Golden Hamster with non-alcoholic fatty liver disease Induced by High-fat Diet

| Group (n = 10) | Dose mg/kg | TG (mol/g protein) | TC (mol/g protein) |
|---|---|---|---|
| Normal Group | — | 2.0 ± 0.3 | 1.8 ± 0.6 |
| Model Group | — | 4.6 ± 0.8*** | 4.9 ± 1.3** |
| Simvastatin Group | 3 | 3.0 ± 0.8## | 2.7 ± 0.9## |
| IMM-H007 | 50 | 3.6 ± 0.1# | 2.8 ± 0.8# |
|  | 100 | 3.3 ± 0.1## | 2.4 ± 0.4## |
|  | 200 | 2.8 ± 0.1### | 1.8 ± 0.8## |

***P <0.001, compared with normal group;
P <0.001,
P <0.01,
P <0.05 compared with model group

3.5 Liver MRI Analysis

Figure 5:
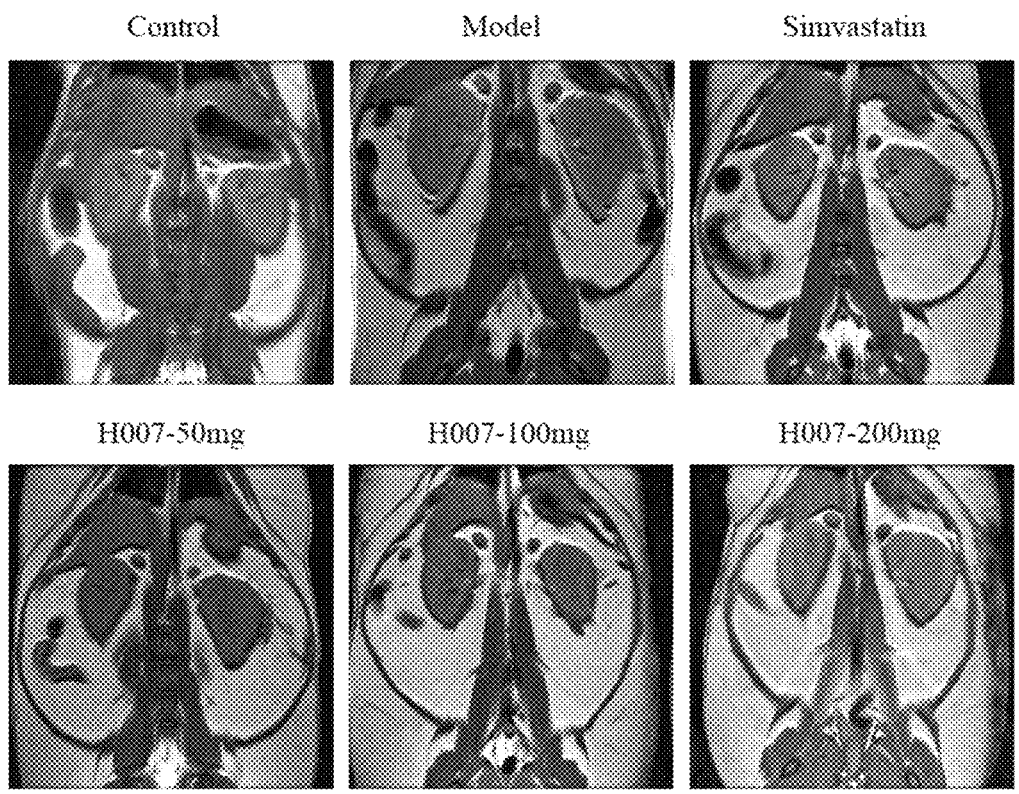
FIG. 5 is a nuclear magnetic imaging diagram of golden hamsters in the experimental example of the present invention.

The results of MR examination showed that the subcutaneous and abdominal adipose in the golden hamster of the model group was significantly increased compared with the normal group, and subcutaneous and abdominal adipose was reduced after administration of simvastatin and IMM-H007 (FIG. 5).

3.6 Pathological Observation of Liver Tissue

Figure 6:
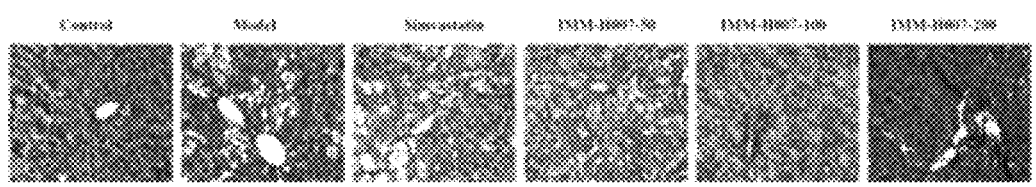
FIG. 6 is a comparison of HE pathological staining results of liver tissues of golden hamsters in various experimental groups of the present invention.

From the results of HE staining shown in FIG. 6, in the normal animals, the liver cells were arranged radially around the central vein, and the collagenous fibers were regularly distributed in the central vein and other blood vessel walls; in the animals of the model group, the liver cells appeared vacuolated, and collagenous fibers appeared between the liver cells with irregular distribution; and in the animals of the simvastatin group, vacuoles appeared in the liver cells, and collagenous fibers appeared between the liver cells and showed an irregular distribution. In each dose group of IMM-H007, the liver cells were arranged radially around the central vein, and collagenous fibers were regularly distributed in the central vein and the hepatic lobule border zone.

Figure 7:
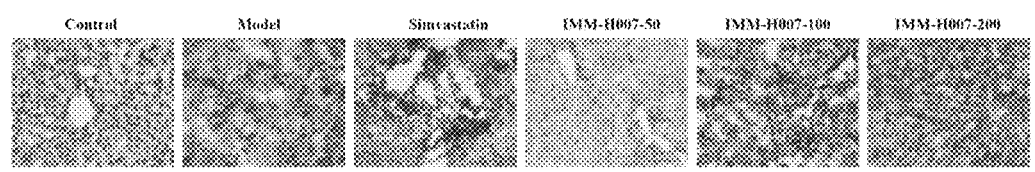
FIG. 7 is a comparison of the Oil Red O staining results of liver tissues of golden hamsters in various experimental groups of the present invention.

From the results of Oil Red O staining (FIG. 7), in the normal animals, the liver cells were arranged radially around the central vein and contained less intracellular neutral fat; in the animals of the high-fat diet group, there was a lot of fat deposition and vacuolization in the liver cells; and in the animals of the simvastatin group, there was fat deposition and large necrosis in the liver cells. In the animals of each dose group of IMM-H007, fat deposition was also observed in the liver cells, but it was significantly reduced compared with the model group.

In summary, triacetyl-3-hydroxyphenyladenosine (IMM-H007) can significantly reduce the blood lipid level of the golden hamsters with non-alcoholic fatty liver disease, significantly reduce AST and ALT levels, and significantly improve liver function, suggesting that IMM-H007 can be used to prepare a pharmaceutical drug for preventing or treating non-alcoholic fatty liver disease.

The invention claimed is:

1. A method of treating non-alcoholic fatty liver disease comprising administering to a human or an animal in need thereof a pharmaceutical composition comprising 2', 3', 5',-tri-O-acetyl-$N^6$ (3-hydroxylphenyl)adenosine as shown in formula (I) or a pharmaceutically acceptable salt thereof, and a pharmaceutically acceptable carrier,

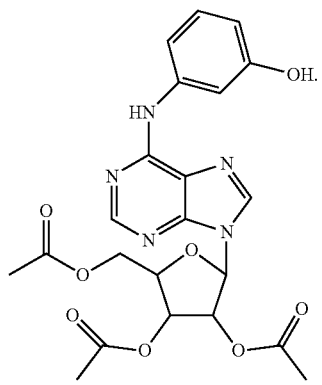

(I)

2. The method of claim 1, wherein the non-alcoholic fatty liver disease is a fatty liver disease caused by a high-calorie diet.

3. The method of claim 1, wherein the pharmaceutical composition further comprises a pharmaceutically acceptable carrier.

4. The method of claim 3, wherein the pharmaceutical composition is in a form selected from the group consisting of a tablet, a capsule, a pill or an injection.

5. The method of claim 3, wherein the pharmaceutical composition is selected from the group consisting of a sustained release preparation, a controlled release preparation and a microparticle drug delivery system.

6. The method of claim 3, wherein the pharmaceutical composition is administered in a dose of from 0.001 to 150 mg/kg.

7. The method of claim 3, wherein the pharmaceutical composition is administered in a dose of from 0.1 to 100 mg/kg.

8. The method of claim 3, wherein the pharmaceutical composition is administered in a dose of from 1 to 60 mg/kg.

9. The method of claim 3, wherein the pharmaceutical composition is administered in a dose of from 2 to 30 mg/kg.

* * * * *